United States Patent [19]

Kiehs et al.

[11] 4,190,650

[45] Feb. 26, 1980

[54] PHOSPHONYL VINYL PHOSPHORUS COMPOUNDS AS PESTICIDES

[75] Inventors: Karl Kiehs, Lampertheim; Hans J. Schrepfer, Ludwigshafen; Heinrich Adolphi, Limburgerhof, all of Fed. Rep. of Germany

[73] Assignee: BASF Aktiengesellschaft, Fed. Rep. of Germany

[21] Appl. No.: 889,834

[22] Filed: Mar. 24, 1978

[30] Foreign Application Priority Data

Apr. 9, 1977 [DE] Fed. Rep. of Germany ....... 2715924

[51] Int. Cl.$^2$ ............................ A01N 9/36; C07F 9/40
[52] U.S. Cl. ...................................... 424/204; 260/931
[58] Field of Search .......................... 260/931; 424/204

[56] References Cited

U.S. PATENT DOCUMENTS

| | | | |
|---|---|---|---|
| 2,578,652 | 12/1951 | Cassaday | 260/942 |
| 3,476,838 | 11/1969 | Miller et al. | 260/931 |
| 3,594,454 | 7/1971 | Beriger et al. | 260/941 |
| 3,781,426 | 12/1973 | Beriger et al. | 424/212 |

OTHER PUBLICATIONS

Pudovik, "Chem. Abstracts", vol. 51 (1965), p. 1827a.

*Primary Examiner*—Anton H. Sutto
*Attorney, Agent, or Firm*—Keil & Witherspoon

[57] ABSTRACT

New phosphoric acid derivatives and pesticides containing these phosphoric acid derivatives as active ingredients. The new active ingredients are obtained by reaction of α-formylalkylphosphonic acid esters with phosphoric (phosphonic) acid ester halides or by reaction of α-formyl-α-haloalkylphosphonic acid esters with phosphites.

The compounds are suitable for combatting pests from the classes of insects, Arachnida and nematodes in the crop protection, hygiene, stores protection and veterinary sectors.

6 Claims, No Drawings

PHOSPHONYL VINYL PHOSPHORUS COMPOUNDS AS PESTICIDES

The present invention relates to new phosphoric acid derivatives, processes for their manufacture, and pesticides containing these phosphoric acid derivatives as active ingredients.

The phosphoric acid derivatives according to the invention have the formula

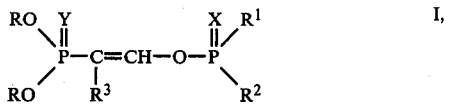

where R denotes linear or branched alkyl of a maximum of 6 carbon atoms, $R^1$ denotes linear or branched alkyl or alkoxy of a maximum of 6 carbon atoms, linear or branched alkynyloxy of a maximum of 4 carbon atoms, phenyl, phenyl mono- or polysubstituted by halogen or alkyl of 1 to 4 carbon atoms, or benzyloxy, $R^2$ denotes alkoxy, alkylthio, alkylamino or dialkylamino, (alkyl in these radicals being linear or branched and of a maximum of 6 carbon atoms), linear of branched alkynyloxy of a maximum of 4 carbon atoms, or benzyloxy, $R^3$ denotes hydrogen or linear or branched alkyl of a maximum of 3 carbon atoms, X denotes oxygen or sulfur, and Y denotes oxygen or sulfur.

The new phosphoric acid esters are outstandingly suitable for combatting important pests from the classes of insects, Arachnida and nematodes.

Examples of linear or branched alkyl for R and $R^1$ in formula I are methyl, ethyl and isomeric propyl, butyl, pentyl and hexyl; examples of linear or branched alkoxy for $R^1$ and $R^2$ are methoxy, ethoxy and isomeric propoxy, butoxy, pentoxy and hexoxy; examples of linear or branched alkynyloxy for $R^1$ and $R^2$ are propyn-2-yloxy, butyn-2-yloxy, butyn-3-yloxy, and 1-methylpropyn-2-yloxy; examples of alkylthio, alkylamino and dialkylamino for $R^2$ are methylthio, ethylthio, n-propylthio, isopropylthio, n-butylthio, sec-butylthio, methylamino, ethylamino, propylamino, isopropylamino, n-butylamino, methylethylamino, dimethylamino, diethylamino, di-n-propylamino, and di-n-butylamino; examples of linear or branched alkyl for $R^3$ are methyl, ethyl, n-propyl, and isopropyl.

Preferred substituents R are methyl, ethyl and isopropyl; preferred substituents $R^1$ are methyl, ethyl, methoxy, ethoxy and phenyl; preferred substituents $R^2$ are methoxy, ethoxy, 1-methylpropyn-2-yloxy, propyn-2-yloxy, methylthio, n-propylthio, sec-butylthio, isobutylthio, isopropylamino and dimethylamino; and preferred substituents $R^3$ are hydrogen and methyl.

Examples of compounds according to the invention are: O,O-dimethyl-O-(2-methyl-2-O,O-dimethylphosphonyl)-vinylphosphate, O,O-diethyl-O-(2-methyl-2O,O-dimethylphosphonyl)-vinylphosphate, O-methyl-O-(2-methyl-2-O,O-dimethylphosphonyl)-vinylmethane phosphonate, O-ethyl-O-(2-methyl-2-O,O-dimethylphosphonyl)-vinylethane phosphonate, O-methyl-O-(2-methyl-2-O,O-dimethylphosphonyl)-vinlyphenyl phosphonate, O-ethyl-S-n-propyl-O-(2-methyl-2-O,O-dimethylphosphonyl)-vinyl thiophosphate, O-ethyl-S-sec.-butyl-O-(2-methyl-2-O,O-dimethylphosphonyl)-vinyl thiophosphate, O-methyl-S-methyl-O-(2-methyl-2-O,O-dimethylphosphonyl)-vinyl thiophosphate, O-methyl-N,N-dimethyl-O-(2-methyl-O,O-dimethylphosphonyl)-vinylphosphoric acid amide, O-ethyl-N-isopropyl-O-(2-methyl-2-O,O-dimethylphosphonyl)-vinylphosphoric acid amide, O,O-dimethyl-O-(2-methyl-2-O,O-dimethylphosphonyl)-vinylthiophosphate, O,O-diethyl-O-(2-methyl-2-O,O-dimethylphosphonyl)-vinylthiophosphate, O-ethyl-O-(2-methyl-2-O,O-dimethylphosphonyl)-vinylethane thiophosphonate, O-methyl-O-(2-methyl-2-O,O-dimethylphosphonyl)-vinylphenyl thiophosphonate, N,N-dimethyl-O-(2-methyl-2-O,O-dimethylphosphonyl)-vinylphenylthiophosphonic acid amide, O-methyl-S-n-propyl-O-(2-methyl-2-O,O-dimethylphosphonyl)-vinyl dithiophosphate, O-ethyl-S-n-propyl-O-(2-methyl-2-O,O-dimethylphosphonyl)-vinyl dithiophosphate, O-methyl-S-sec.-butyl-O-(2-methyl-2-O,O-dimethylphosphonyl)-vinyl dithiophosphate, O-ethyl-S-sec.-butyl-O-(2-methyl-2-O,O-dimethylphosphonyl)-vinyl dithiophosphate, O-methyl-N,N-dimethyl-O-(2-methyl-2O,O-dimethylphosphonyl)-vinyl thiophosphoric acid amide, O-ethyl-N,N-dimethyl-O-(2-methyl-2O,O-dimethylphosphonyl)-vinylthiophosphoric acid amide, O-ethyl-N-isopropyl-O-(2-methyl-2-O,O-dimethylphosphonyl)-vinylthiophosphoric acid amide, O-propyn-2-yl-O-(2-methyl-2-O,O-dimethylphosphonyl)-vinylmethane thiophosphonate, O,O-dimethyl-O-(2-methyl-2-O,O-dimethylthiophosphonyl)-vinyl phosphate, O,O-diethyl-O-(2-methyl-2-O,O-dimethylthiophosphonyl)-vinyl phosphate, O-ethyl-O-(2-methyl-2-O,O-dimethylthiophosphonyl)-vinylmethane phosphate, O-ethyl-O-(2-methyl-2-O,O-dimethylthiophosphonyl)-vinylethane phosphate, O-ethyl-S-n-propyl-O-(2-methyl-2-O,O-dimethylthiophosphonyl)thiophosphate, O-methyl-N,N-dimethyl-O-(2-methyl-2-O,O-dimethylthiophosphonyl)-vinylphosphoric acid amide, O-ethyl-N-isopropyl-O-(2-methyl-2-O,O-dimethylthiophosphonyl)-vinylphosphoric acid amide, O,O-dimethyl-O-(2-methyl-2-O,O-dimethylthiophosphonyl)-vinyl thiophosphate, O,O-diethyl-O-(2-methyl-2-O,O-dimethylthiophosphonyl)-vinyl thiophosphate, O-ethyl-O-(2-methyl-2O,O-dimethylthiophosphonyl)-vinylmethane thiophosphonate, O-ethyl-O-(2-methyl-2-O,O-dimethylthiophosphonyl)-vinylethane thiophosphonate, O-ethyl-S-n-propyl-O-( 2-methyl-2-O,O-dimethylthiophosphonyl)-vinyl dithiophosphate, O-methyl-S-isobutyl-O-(2-methyl-2-O,O-dimethylthiophosphonyl)-vinyl dithiophosphate, O-ethyl-S-isobutyl-O-(2-methyl-2O,O-dimethylthiophosphonyl)-vinyl dithiophosphate, O-ethyl-S-sec.-butyl-O-(2-methyl-2-O,O-dimethylthiophosphonyl)-vinyl dithiophosphate, O-methyl-S-methyl-O-(2-methyl-2O,O-dimethylthiophosphonyl)-vinyl dithiophosphate, O-methyl-N,N-dimethyl-O-(2-methyl-2-O,O-dimethylthiophosphonyl)-vinylthiophosphoric acid amide, O-ethyl-N-isopropyl-O-(2-methyl-2-O,O-dimethylthiophosphonyl)-vinylthiophosphoric acid amide, O-propyn-2-yl-O-(2-methyl-2-O,O-dimethylphosphonyl)-vinylmethane thiophosphonate, O,O-dimethyl-O-(2-ethyl-2-O,O-dimethylphosphonyl)-vinyl phosphate, O,O-diethyl-O-(2-ethyl-2-O,O-dimethylphosphonyl)-vinyl phosphate, O-methyl-O-(2-ethyl-2-O,O-dimethylphosphonyl)-vinylmethane phosphonate, O-ethyl-O-(2-ethyl-2-O,O-dimethylphosphonyl)-vinylphenyl phosphonate, O-ethyl-S-n-propyl-O-(2-ethyl-2-O,O-dimethylphosphonyl)-vinyl thiophosphate, O,O-dimethyl-O-(2-ethyl-2-O,O-dimethylphosphonyl)-vinyl thiophosphate, O,O-diethyl-O-(2-ethyl-2-O,O-dimethylphosphonyl)-vinyl thiophosphate, O-ethyl-O-(2-ethyl-2-O,O-dimethylphosphonyl)-vinylethane thiophosphonate, O-ethyl-O-(2-ethyl-2-O,O-dimethylphosphonyl)-vinylphenyl thiophosphonate, O-ethyl-S-n-propyl-O-(2-ethyl-2-O,O-dimethylphosphonyl)-vinyl dithiophosphate, O-methyl-S-methyl-O-(2-ethyl-2-O,O-dimethylphosphonyl)-vinyl dithiophosphate, O-ethyl-N-isopropyl-O-(2-ethyl-2-O,O-dimethylphosphonyl)-vinylthiophosphoric acid amide, O,O-dimethyl-O-(2-ethyl-2-O,O-dimethylthiophosphonyl)-vinyl thiophosphate, O,O-diethyl-O-(2-ethyl-2-O,O-dimethylthiophosphonyl)-vinyl thiophosphate, O-ethyl-O-(2-ethyl-2-O,O-dimethylthiophosphonyl)-vinylethane thiophosphonate, O-methyl-O-(2-ethyl-2-O,O-dimethylthiophosphonyl)-vinylphenyl thiophosphonate, O-ethyl-S-n-propyl-O-(2-ethyl-2-O,O-dimethylthiophosphonyl)-vinylthiophosphate, O-ethyl-S-sec.-butyl-O-(2-ethyl-2-O,O-dimethylphosphonyl)-vinyl thiophosphate, O,O-dimethyl-O-(2-ethyl-2-O,O-dimethylthiophosphonyl)-vinyl thiophosphate, O,O-diethyl-O-( 2-ethyl-2-O,O-dimethylthiophosphonyl)-vinyl thiophosphate, O-ethyl-O-(2-ethyl-2-O,O-dimethylthiophosphonyl)-vinylmethane thiophosphonate, O-methyl-O-(2-ethyl-2-O,O-dimethylthiophosphonyl)-vinylphenyl thiophosphonate, O-ethyl-S-n-propyl-O-(2-ethyl-2-O,O-dimethylthiophosphonyl)-vinyl dithiophosphate, O-ethyl-S-sec.-butyl-O-(2-ethyl-2-O,O-dimethylthiophosphonyl)-vinyl dithiophosphate, O,O-dimethyl-O-(2-O,O-dimethylphosphonyl)-vinyl phosphate, O,O-diethyl-O-(2-O,O-dimethylphosphonyl)-vinyl phosphate, O-ethyl-O-(2-O,O-dimethylphosphonyl)-vinylmethane phosphonate, O-methyl-O-(2-O,O-dimethylphosphonyl)-vinylphenyl phosphonate, O-methyl-S-n-propyl-O-(2-O,O-dimethylphosphonyl)-vinyl thiophosphate, O-ethyl-S-n-propyl-O-(2-O,O-dimethylphosphonyl)-vinyl thiophosphate, O-ethyl-S-isobutyl-O-(2-O,O-dimethylphosphonyl)-vinyl thiophosphate, O-ethyl-S-sec.-butyl-O-(2-O,O-dimethylphosphonyl)-vinyl thiophosphate, O-methyl-S-methyl-O-(2-O,O-dimethylphosphonyl)-vinyl thiophosphate, O-methyl-N,N-dimethyl-O-(2O,O-dimethylphosphonyl)-vinylphosphoric acid amide, O-ethyl-N-isopropyl-O-(2-O,O-dimethylphosphonyl)-vinylphosphoric acid amide, O,O-dimethyl-O-(2-O,O-dimethylphosphonyl)-vinyl thiophosphate, O,O-diethyl-O-(2-O,O-dimethylphosphonyl)-vinyl thiophosphate, O-methyl-O-(2-O,O-dimethylphosphonyl)-vinylmethane thiophosphonate, O-methyl-O-(2-O,O-dimethylphosphonyl)-vinylphenyl thiophosphonate, O-methyl-S-n-propyl-O-(2-O,O-dimethylphosphonyl)-vinyl dithiophosphate, O-ethyl-S-n-propyl-O-(2-O,O-dimethylphosphonyl)-vinyl dithiophosphate, O-ethyl-S-isobutyl-O-(2-O,O-dimethylphosphonyl)-vinyl dithiophosphate, O-methyl-S-sec.-butyl-O-(2-O,O-dimethylphosphonyl)-vinyl dithiophosphate, O-ethyl-S-sec.-butyl-O-(2-O,O-dimethylphosphonyl)-vinyl dithiophosphate, O-methyl-S-methyl-O-(2-O,O-dimethylphosphonyl)-vinyl dithiophosphate, O-ethyl-N,N-dimethyl-O-(2-O,O-dimethylphosphonyl)-vinylthiophosphoric acid amide, O-ethyl-N-isopropyl-O-(2-O,O-dimethylphosphonyl)-vinylthiophosphoric acid amide, O-propyn-2-yl-O-(2-O,O-dimethylphosphonyl)-vinylmethane thiophosphonate, O-(2-methylpropyn-2-yl)-O-(2-O,O-dimethylphosphonyl)-vinylmethane thiophosphonate, O,O-dimethyl-O-(2-O,O-dimethylthiophosphonyl)-vinyl phosphate, O,O-diethyl-O-(2-O,O-dimethylthiophosphonyl)-vinyl phosphate, O-ethyl-O-(2-O,O-dimethylthiophosphonyl)-vinylmethane phosphonate, O-methyl-O-(2-O,O-dimethylthiophosphonyl)-vinylphenyl phosphonate, O-ethyl-S-n-propyl-O-(2-O,O-dimethylthiophosphonyl)-vinyl thiophosphate, O-methyl-N,N-dimethyl-O-(2-O,O-dimethylthiophosphonyl)-vinylphosphoric acid amide, O-ethyl-N-isopropyl-O-(2-O,O-dimethylthiophosphonyl)-vinylphosphoric acid amide, O,O-dimethyl-O-(2-O,O-dimethylthiophosphonyl)-vinyl thiophosphate, O-ethyl-O-(2-O,O-dimethylthiophosphonyl)-vinylmethane thiophosphonate, O-ethyl-S-n-propyl-O-(2-O,O-dimethylthiophosphonyl)-vinyl dithiophosphate, O-methyl-S-sec.-butyl-O-(2-O,O-dimethylthiophosphonyl)-vinyl dithiophosphate, O-methyl-N,N-dimethyl-O-(2,O-dimethylthiophosphonyl)-vinylthiophosphoric acid amide, O-propyn-2-yl-O-(2-O,O-dimethylthiophosphonyl)-vinylmethane thiophosphonate, O,O-dimethyl-O-(2-methyl-2-O,O-diethylphosphonyl)-vinyl phosphate, O-ethyl-O-(2-methyl-2-O,O-diethylphosphonyl)-vinylmethane phosphonate, O-ethyl-O-(2-methyl-2-O,O-diethylphosphonyl)-vinylethane phosphonate, O-methyl-O-(2-2-methyl-2-O,O-diethylphosphonyl)-vinylphenyl phosphonate, O-ethyl-S-n-propyl-O-(2-methyl-2-O,O-diethylphosphonyl)-vinyl thiophosphate, O-ethyl-N,N-dimethyl-O-(2-methyl-2-O,O-diethylphosphonyl)-vinylphosphoric acid amide, O,O-diethyl-O-(2-methyl-2-O,O-diethylphosphonyl)-vinyl thiophosphate, O-methyl-O-(2-methyl-2-O,O-diethylphosphonyl)-vinylphenyl phosphonate, O-methyl-S-n-propyl-O-(2-methyl-2-O,O-diethylphosphonyl)-vinyl thiophosphate, O-ethyl-S-n-propyl-O-(2-methyl-2-O,O-diethylphosphonyl)-vinyl thiophosphate, O-ethyl-S-isobutyl-O-(2-methyl-2-O,O-diethylphosphonyl)-vinyl thiophosphate, O-methyl-N,N-dimethyl-O-(2-methyl-2-O,O-diethylphosphonyl)-vinylthiophosphoric acid amide, O-propyn-2-yl-O-(2-methyl-2-O,O-diethylphosphonyl)-vinylmethane thiophosphonate, O,O-dimethyl-O-(2-methyl-2-O,O-diethylthiophosphonyl)-vinyl phosphate, O,O-diethyl-O-(2-methyl-2-O,O-diethylthiophosphonyl)-vinyl phosphate, O-methyl-O-(2-methyl-2-O,O-diethylthiophosphonyl)-vinylphenyl phosphonate, O-methyl-N,N-dimethyl-O-(2-methyl-2-O,O-diethylthiophosphonyl)-vinylphosphoric acid amide, O-ethyl-N-isopropyl-O-(2-methyl- 2-O,O-diethylthiophosphonyl)-vinylphosphoric acid amide, O,O-dimethyl-O-(2-methyl-2-O,O-diethylthiophosphonyl)-vinyl thiophosphate, O,O-diethyl-O-(2-methyl-2-O,O-diethylthiophosphonyl)-vinyl thiophosphate, O-ethyl-O-(2-methyl-2-O,O-diethylthiophosphonyl)-vinylmethane thiophosphonate, O-methyl-O-(2-methyl-2-O,O-diethylthiophosphonyl)-vinylethane thiophosphonate, O-methyl-S-n-propyl-O-(2-methyl-2-O,O-diethylthiophosphonyl)-vinyl dithiophosphate, O-ethyl-S-isobutyl-O-(2-methyl-2-O,O-diethylthiophosphonyl)-vinyl dithiophosphate, O-methyl-N,N-dimethyl-O-(2-methyl-2-O,O-diethylthiophosphonyl)-vinylthiophosphoric acid amide, O-ethyl-O-(2-methyl-2-O,O-diethylthiophosphonyl)-vinylthiophosphoric acid amide, O,O-dimethyl-O-(2-ethyl-2-O,O-diethylphosphonyl)-vinyl phosphate, O,O-diethyl-O-(2-ethyl-2-O,O-diethylphosphonyl)-vinyl phosphate, O-ethyl-O-(2-ethyl-2-O,O-diethylphosphonyl)-vinylphenyl phosphonate, O-ethyl-S-n-propyl-O-(2-ethyl-2-O,O-diethylphosphonyl)vinyl thiophosphate, O-methyl-N,N-dimethyl-O-(2-ethyl-2-O,O-diethylphosphonyl)-vinylphosphoric acid amide, O-ethyl-N-isopropyl-O-(2-ethyl-2-O,O-diethylphosphonyl)-vinylphosphoric acid amide, O,O-dimethyl-O-(2-ethyl-2-O,O-diethylphosphonyl)-vinyl thiophosphate, O,O-diethyl-O-(2-O,O-diethylphosphonyl)-vinyl thiophosphate, O-ethyl-O-(2-ethyl-2-O,O-diethylphosphonyl)-vinylmethane thiophosphonate, O-ethyl-O-(2-ethyl-2-O,O-diethylphosphonyl)-vinylmethane thiophosphonate, O-ethyl-O-(2-ethyl-2-O,O-diethylphosphonyl)-vinylphenyl thiophosphonate, O-methyl-S-n-propyl-O-(2-ethyl-2-O,O-diethylphosphonyl)-vinyl dithiophosphate, O-ethyl-S-sec.-butyl-O-(2-ethyl-2-O,O-diethylphosphonyl)-vinyl dithiophosphate, O-ethyl-N,N-diethyl-O-(2-ethyl-2-O,O-diethylphosphonyl)-vinylthiophosphoric acid amide, O-methyl-N-isopropyl-O-(2-ethyl-2-O,O-diethylphosphonyl)-vinylthiophosphoric acid amide, O-1-methylpropyn-2-yl-O-(2-ethyl-2-O,O-diethylphosphonyl)-vinylmethane thiophosphonate, O,O-dimethyl-O-(2-ethyl-2-O,O-diethylthiophosphonyl)-vinyl phosphate, O,O-diethyl-O-(2-ethyl-2-O,O-diethylthiophosphonyl)-vinyl phosphate, O-methyl-O-(2-ethyl-2-O,O-diethylthiophosphonyl)-vinylphenyl phosphonate, O-methyl-N,N-dimethyl-O-(2-ethyl-2-O,O-diethylthiophosphonyl)-vinyl-phosphoric acid amide, O-ethyl-N-isopropyl-O-(2-ethyl-2-O,O-diethylthiophosphonyl)-vinylphosphoric acid amide, O,O-dimethyl-O-(2-ethyl-2-O,O-diethylthiophosphonyl)-vinyl thiophosphate, O,O-diethyl-0-(2-ethyl-2-O,O-diethylthiophosphonyl)-vinyl thiophosphate, O-ethyl-O-(2-ethyl-2-O,O-diethylthiophosphonyl)-vinylphenyl thiophosphonate, O-ethyl-S-n-propyl-O-(2-ethyl-2-O,O-diethylthiophosphonyl)-vinyl dithiophosphate, O-methyl-N,N-dimethyl-O-(2-ethyl-2-O,O-diethylthiophosphonyl)-vinylphosphoric acid amide, O-propyn-2-yl-O-(2-ethyl-2-O,O-diethylthiophosphonyl)-vinylmethane thiophosphonate, O,O-dimethyl-O-(2-O,O-diethylphosphonyl)-vinyl phosphate, O-methyl-O-(2-O,O-diethylphosphonyl)-vinylphenyl phosphate, O-ethyl-S-n-propyl-(2-O,O-diethylphosphonyl)-vinyl thiophosphate, O-methyl-N,N-dimethyl-O-(2-O,O-diethylphosphonyl)-vinylphosphoric acid amide, O-ethyl-O-(2-O,O-diethylphosphonyl)-vinylmethane thiophosphonate, O-ethyl-O-(2-O,O-diethylphosphonyl)-vinylethane thiophosphonate, O-ethyl-S-n-propyl-O-(2-O,O-diethylphosphonyl)-vinyl dithiophosphate, O-ethyl-bis-sec.-butyl-O-(2-O,O-diethylphosphonyl)-vinyl dithiophosphate, O-methyl-S-methyl-O-(2-O,O-diethylphosphonyl)-vinyl dithiophosphate, O-methyl-N,N-dimethyl-O-(2-O,O-diethylphosphonyl)-vinylthiophosphoric acid amide, O-propyn-2-yl-O-(2-O,O-diethylphosphonyl)-vinylmethane thiophosphonate, O,O-dimethyl-O-(2-O,O-diethylthiophosphonyl)-vinyl phosphate, O,O-diethyl-O-(2-O,O-diethylthiophosphonyl)-vinyl phosphate, O-methyl-O-(2-O,O-diethylthiophosphonyl)-vinylphenyl phosphonate, O-ethyl-S-n-propyl-O-(2-O,O-diethylthiophosphonyl)-vinyl thiophosphate, O-ethyl-N-isopropyl-O-(2-O,O-diethylthiophosphonyl)-vinylphosphoric acid amide, O,O-dimethyl-O-(2-O,O-diethylthiophosphonyl)-vinyl thiophosphate, O,O-diethyl-O-(2-O,O-diethylthiophosphonyl)-vinyl thiophosphate, O-methyl-O-(2-O,O-diethylthiophosphonyl)-vinylmethane thiophosphonate, O-ethyl-O-(2-O,O-diethylthiophosphonyl)-vinylmethane thiophosphonate, O-methyl-O-(2-O,O-diethylthiophosphonyl)-vinylphenyl thiophosphonate, O-methyl-S-n-propyl-O-(2-O,O-diethylthiophosphonyl)-vinyl dithiophosphate, O-ethyl-S-isobutyl-O-(2-O,O-diethylthiophosphonyl)-vinyl dithiophosphate, O-methyl-N,N-dimethyl-O-(2-O,O-diethylthiophosphonyl)-vinylthiophosphoric acid amide, O-propyn-2-yl-O-(2-O,O-diethylthiophosphonyl)-vinylthiophosphonate, O,O-dimethyl-O-(2-methyl-2-O,O-diisopropylphosphonyl)-vinyl phosphate, O,O-diethyl-O-(2-methyl-2-O,O-diisopropylthiophosphonyl)-vinyl phosphate, O-methyl-N,N-dimethyl-O-(2-methyl-2-O,O-diisopropylphosphonyl)-vinylphosphoric acid amide, O-1-methylpropyn-2-yl-O-(2-methyl-2-O,O-diisopropylphosphonyl)-vinylmethane phosphonate, O-methyl-S-ethyl-(2-methyl-2-O,O-diisopropylphosphonyl)-vinyl thiophosphate, O-benzyl-O-methyl-O-(2-methyl-2-O,O-dimethylphosphonyl)-vinyl phosphate, O-benzyl-O-ethyl-O-(2-methyl-2-O,O-dimethylphosphonyl)-vinyl phosphate, O-benzyl-O-methyl-O-(2-ethyl-2-O,O-dimethylphosphonyl)-vinyl phosphate, O-benzyl-O-methyl-O-(2-O,O-dimethylthiophosphonyl)-vinyl phosphate, O,O-dimethyl-O-(2-isopropyl-2-O,O-dimethylphosphonyl)-vinyl phosphate, O,O-diethyl-O-(2-isopropyl-2-O,O-dimethylphosphonyl)-vinyl phosphate, O-methyl-O-(2-isopropyl-2-O,O-dimethylphosphonyl)-vinylmethane phosphonate, O-ethyl-O-(2-isopropyl-2-O,O-dimethylphosphonyl)-vinylethane phosphonate, O-ethyl-S-n-propyl-O-(2-isopropyl-2-O,O-diethylphosphonyl)-vinyl thiophosphate, N,N-dimethyl-O-(2-isopropyl-2-O,O-dimethylphosphonyl)-vinylmethane phosphonic acid amide, O-methyl-N,N-dimethyl-O-(2-isopropyl-2-O,O-dimethylphosphonyl)-vinylphosphoric acid amide, O-ethyl-N,N-dimethyl-O-(2-isopropyl-2-O,O-diethylphosphonyl)-vinylthiophosphoric acid amide, O-methyl-N-ethyl-O-(2-isopropyl-2-O,O-diethylthiophosphonyl)-vinylthiophosphoric acid amide, O-methyl-S-methyl-O-(2-isopropyl-2-O,O-dimethylthiophosphonyl)-vinyl dithiophosphate, and O-ethyl-S-n-propyl-O-(2-isopropyl-2-O,O-dimethylphosphonyl)-vinyl dithiophosphate.

The present invention further relates to processes for the manufacture of the new phosphoric acid derivatives of the formula I.

Phosphoric acid derivatives of the formula I may be obtained by reaction of α-formylalkyl phosphonic acid esters of the formula

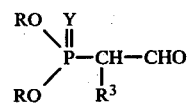

with (thiono-) (thiolo-) (phosphoric) (phosphonic) acid ester halides or ester amide halides of the formula

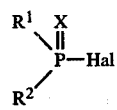

in the presence of acid acceptors or using alkali metal, alkaline earth metal or ammonium salts of α-formylalkyl phosphonic acid esters of the formula II. In formulae II and III, R, $R^1$, $R^2$, $R^3$, X and Y have the above meanings, and Hal denotes halogen, especially chlorine and bromine.

As acid acceptors, all conventional acid binders may be used, e.g., alkali metal carbonates, hydroxides, hydrides and alcoholates, such as sodium and potassium carbonate, sodium and potassium methylate or ethylate, further, aliphatic, aromatic or heterocyclic amines, e.g., triethylamine, trimethylamine, dimethylaniline, diethylaniline, triethylenediamine, dimethylbenzylamine and pyridine. Aqueous alkali metal hydroxide solutions and alkali metal alcoholates have proved to be particularly suitable.

The reaction temperature may be varied within a large range; in general, the reaction is carried out at from 0° to 150° C., preferably from room temperature to 90° C.

The reaction is advantageously carried out in suitable solvents or diluents. Practically all inert organic solvents are suitable, e.g., nitriles, such as acetonitrile and propionitrile; ketones, such as acetone, methyl ethyl ketone and methyl isopropyl ketone; ethers, such as diethyl ether, dioxane and tetrahydrofuran; aliphatic and aromatic, optionally chlorinated, hydrocarbons, such as benzene, toluene, xylenes, chlorobenzenes, methylene chloride, chloroform and carbon tetrachloride; amides, such as dimethylformamide and N-methylpyrrolidone; and dimethyl sulfoxide.

The reaction may also be carried out in a two-phase medium, for example when using solvents mentioned above which are immiscible with water, and aqueous alkali metal hydroxide solutions as acid acceptors. In such cases, a phase transfer catalyst, e.g., triethylbenzylammonium chloride, trimethylbenzylammonium bromide, triphenylbenzylammonium chloride, methyltributylammonium iodide and tetrabutylammonium bisulfate, may, if desired, be added.

The α-formylalkyl phosphonic acid esters of the formula II may be prepared by acid hydrolysis of 2-alkoxy-1-alkylvinyl- or 2-alkoxyvinylphosphonic acid esters (Ann. Chem., 751, 69–72, 1971; J. Gen. Chem. USSR, 41, 1687–1691, 1971). α-formylethanephosphonic acid esters of the formula II in which Y is oxygen and $R^3$ is methyl may also be obtained by hydroformylation of vinylphosphonic acid esters of the formula

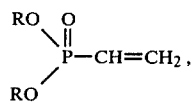

where R has the above meanings, with carbon monoxide and hydrogen in the presence of conventional rhodium-containing hydroformylation catalysts (cf. German Patent Application P 27 15 923).

The (thiono-) (thiolo-) (phosphoric) (phosphonic) acid ester halides or ester amide halides of the formula III to be used as starting materials are known and may be prepared by methods disclosed in the literature.

Individual examples of starting materials III are as follows: O,O-dimethyl-, O,O-dimethoxymethyl-, O,O-diethyl-, O,O-di-(2-chloroethyl)-, O,O-di-(2-methoxyethyl)-, O,O-di-(2-ethoxyethyl)-, O,O-di-n-propyl-, O,O-diisopropyl-, O-methyl-O-ethyl-, O-methyl-O-n-propyl-, O-methyl-O-isopropyl-, O-ethyl-O-n-propyl-, O-ethyl-O-isopropyl-, O-methyl-O-n-butyl-, O,O-di-n-butyl-, O,O-diisobutyl-, O,O-di-sec-butyl-, O,O-di-tert-butyl-, O-ethyl-O-n-butyl-, O-ethyl-O-sec-butyl-, O-ethyl-O-isobutyl- or O-n-propyl-O-tert.-butyl-(thiono)-phosphoric acid ester chloride, N-methyl-O-methyl-, N-methyl-O-ethyl-, N,N-dimethyl-O-methyl, N,N-dimethyl-O-ethyl-, N-isopropyl-O-methyl-, N-isopropyl-O-ethyl-, N-n-propyl-O-methyl- or N-n-propyl-O-ethyl-(thiono)-phosphoric acid ester amide chloride, O-methylmethane-, O-ethylmethane-, O-propyn-(2)-yl-(1)-methane-, O-methylethane-, O-ethylethane-, O-propyn-(2)-yl-(1)-ethane-, O-methyl-n-propane-, O-methylisopropane-, O-ethyl-n-propane-, O-ethylisopropane-, O-methyl-n-butane-, O-methylisobutane-, O-methyl- sec.-butane-, O-methyl-tert.-butane-, O-ethyl-n-butane-, O-ethylisobutane-, O-ethyl-sec.-butane-, O-ethyl-tert.-butane-, O-methylbenzene and O-ethylbenzene-(thiono)-phosphonic acid ester chloride, O-methyl-S-methyl-, O-ethyl-S-methyl-, O-methyl-S-ethyl-, O-methyl-S-n-propyl-, O-ethyl-S-n-propyl-, O-methyl-S-isopropyl-, O-ethyl-S-isopropyl-, O-methyl-S-n-butyl-, O-ethyl-S-n-butyl-, O-methyl-S-isobutyl-, O-ethyl-S-isobutyl-, O-methyl-S-sec.-butyl-, O-ethyl-S-sec.-butyl-, O-methyl-S-tert.-butyl-, O-ethyl-S-tert.-butyl-, O-methyl-S-allyl-, O-ethyl-S-allyl-, O-methyl-S-propyn-(2)-yl-(1)-, O-ethyl-S-propyn-(2)-yl-(1)-, O-methyl-S-[1-methoxypropyl-(2)]-, O-ethyl-S-[1-methoxypropyl-(2)]-, O-methyl-S-sec.-butynyl- and O-ethyl-S-sec.-butynyl-thio- or -dithiophosphoric acid ester chloride.

In general, the starting materials are employed in equimolar amounts. An excess of the one or the other component generally offers no decisive advantages. The reaction is preferably carried out in the presence of one of the abovementioned solvents, optionally in the presence of an acid acceptor, at the stated temperatures. After a reaction period of from one to several hours, usually at elevated temperatures, the reaction bath is cooled to room temperature. Water-miscible solvents are distilled off under reduced pressure and replaced by an inorganic solvent immiscible with water, e.g., ether or toluene. The organic phase is then worked up in a conventional manner, e.g., washing, drying and distillation.

The new compounds are often obtained as oils which usually cannot be distilled without decomposition occurring, but which, when subjected to incipient distillation, i.e., heating for a fairly long time at reduced pressure at moderately elevated temperatures, are freed from residual volatiles and thus purified. Elemental analysis and infrared and nmr spectroscopic data may be used to identify the compounds.

Further, we have also found a process for the manufacture of phosphoric acid derivatives of the formula I in which R, $R^3$ and Y have the above meanings, X denotes oxygen, and $R^1$ and $R^2$ are identical and denote the radical $OR^4$, $R^4$ denoting linear or branched alkyl of from 1 to 4 carbon atoms or benzyl, by reaction of α-formyl-α-haloalkylphosphonic acid esters of the formula

where R, $R^3$ and y have the above meanings and Hal denotes halogen, especially chlorine and bromine, with phosphites of the formula

    V, where $R^4$ has the above meaning.

The reaction may if desired be carried out in the presence of an indifferent solvent or diluent. Preferably, aromatic hydrocarbons, such as toluene, benzene and xylene, are used.

The reaction temperature may be varied within a wide range. Generally, the range is from 0° to 200° C., preferably from 80° to 160° C.

The starting materials are employed in a molar ratio of 1:1; to ensure substantially complete reaction of compound IV, the phosphites of the formula V may also be employed in excess.

The α-formyl-α-haloalkylphosphonic acid esters of the formula IV may be prepared by halogenation of α-formylalkylphosphonic acid esters of the formula II, if desired in the presence of a solvent.

Examples of halogenating agents are chlorine, bromine, sulfuryl chloride, N-chlorosuccinimide, N-bromosuccinimide, N-chlorophthalimide, N-bromophthalimide, N-chloroacetamide and N-bromoacetamide.

Especially suitable solvents are chlorinated hydrocarbons, such as carbon tetrachloride, chloroform and methylene chloride.

Halogenation is effected at from −50° to +100° C., preferably from 0° C. to room temperature.

To carry out the process, the formyl compound is introduced into the solvent (e.g., chloroform or carbon tetrachloride) and the halogenating agent, e.g., sulfuryl chloride, expediently diluted with the same solvent, is dripped in. After a reaction period of several hours, the solvent is stripped off under reduced pressure, and the residue is taken up in ether, washed with dilute sodium carbonate solution and then with saturated sodium chloride solution, and dried. After stripping off the solvent, the chlorinated product may be further reacted without distillation.

The phosphites of the formula V are known and may be prepared by conventional methods (Houben-Weyl, Methoden der organ. Chemie, 12/2, 53 et seq., Georg Thieme-Verlag, Stuttgart, 1964).

The preparation of the new phosphoric acid derivatives is illustrated in the following examples.

EXAMPLE 1

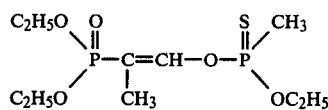

In a 1 liter autoclave equipped with an electromagnetic reciprocating stirrer, 228 g of vinylphosphonic acid diethyl ester and 100 ppm of rhodium as dimeric cyclooctadien-1,5-yl rhodium chloride in 600 ml of toluene as solvent are heated at 80° C. and reacted under a pressure of 600 bars with a mixture of carbon monoxide and hydrogen in a ratio of 1:1. The pressure is maintained for 12 hours by topping up with the gas mixture. The contents are allowed to cool before the pressure on the autoclave is released. The reaction mixture is worked up by distillation. There is obtained 191 g of α-formylethanephosphonic acid diethyl ester; b.p.: 113° C./11 mm Hg.

13.6 g (0.07 mole) of α-formylethanephosphonic acid diethyl ester is refluxed for 2 hours in 100 ml of methanol with 12.6 ml (0.07 mole) of 30% methanolic sodium methylate solution. The solvent is stripped off and the residue is taken up in 100 ml of acetonitrile. 12 g (0.076 mole) of O-ethylmethanethiophosphonyl chloride is added to the suspension and the whole refluxed for 10 hours. After cooling, the precipitate is removed by filtration. The filtrate is concentrated and the residue is taken up in ether, washed with water and dried over sodium sulfate. After stripping off the solvent, the residue is subjected to incipient distillation at 80° C./0.01 mm Hg. There is obtained 19 g (86% of theory) of a pale yellow mobile oil.

$C_{10}H_{22}O_5P_2S$ (316). Calc.: C 38.0; H 7.0; O 19.6; S 10.1. Found: C 37.9; H 7.1; P 19.5; S 10.9.

60 MHz nmr spectrum in $CDCl_3$ (δ values): 1.19–1.50 (9H), 1.74 (3H), 1.89 (3H), 3.73–4.31 (6H), 7.00–7.48 (1H).

EXAMPLE 2

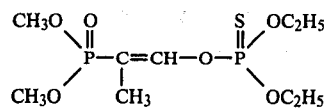

20.4 g (0.11 mole) of O,O-diethylthiophosphoryl chloride is added to a solution of 16.6 g (0.1 mole) of α-formylethanephosphonic acid dimethyl ester in 120 ml of toluene. While stirring vigorously, a solution of 4 g (0.1 mole) of sodium hydroxide in 80 ml of water is dripped in. The reaction mixture is stirred for 12 hours at 70° C. and then cooled. After phase separation the aqueous phase is extracted with toluene. The organic phases are washed with water and dried over sodium sulfate. The solvent is distilled off under reduced pressure and the residue subjected to incipient distillation at 80° C./0.01 mm Hg. There is obtained 16 g (84% of theory) of a yellowish mobile oil.

$C_8H_{20}O_6P_2S$ (318). Calc.: C 34.0; H 6.3; P 19.5; S 10.1. Found: C 33.5; H 6.3; P 19.2; S 10.5.

60 MHz nmr spectrum in $CDCl_3$ (δ values): 1.36 (6H), 1.72 (3H), 3.68 (6), 3.82–4.38 (4H), 6.87–7.19 (1H).

EXAMPLE 3

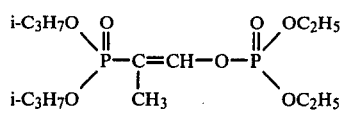

At 10° C., a solution of 14 g (0.104 mole) of sulfuryl chloride in 50 ml of carbon tetrachloride is dripped into a solution of 22.2 g (0.1 mole) of α-formylethanephosphonic acid diisopropyl ester in 150 ml of carbon tetrachloride. The reaction mixture is stirred for 3 hours at room temperature and the solvent is then distilled off under reduced pressure. The residue is taken up in ether, washed with 5% sodium bicarbonate solution and then with saturated sodium chloride solution, and dried over sodium sulfate. The ether is stripped off under reduced pressure. There is obtained 24 g (93.5% of theory) of α-formyl-α-chloroethanephosphonic acid diisopropyl ester.

$C_9H_{18}ClO_4P$ (256.5). Calc.: C 42.1; H 7.1; Cl 13.8; P 12.1. Found: C 42.0; H 7.4; Cl 13.4; P 11.7.

60 MHz nmr spectrum in $CDCl_3$ (δ values): 1.35 (12H), 1.72 (3H), 4.46–5.08 (2H), 9.33 (1H).

Under a nitrogen blanket, 50 ml of triethyl phosphite is added dropwise to 24 g (0.935 mole) of α-formyl-α-chloroethanephosphonic acid diisopropyl ester. The solution is stirred for 1 hour at 100° C. and for 3 hours at reflux temperature. Excess triethyl phosphite is then distilled off at 80° C./0.01 mm Hg. The residue is 31.5 g (93.7% of theory) of a slightly yellow oil.

$C_{13}H_{28}O_7P_2$ (358). Calc.: C 43.6; H 7.9; O 31.3; P 17.3. Found: C 42.6; H 8.2; O 31.6; P 16.8.

60 MHz nmr spectrum in $CDCl_3$ (δ values): 1.12–1.51 (18H), 1.75 (3H), 3.99–4.42 (4H), 4.52–4.82 (2H), 7.04–7.32 (1H).

The following compounds of the formula I may be prepared analogously:

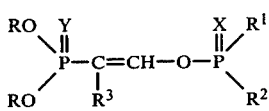

Examples of injurious insects on which the phosphoric acid derivatives according to the invention may be used are as follows:

Lepidoptera order: for example *Plutella maculipennis, Leucoptera coffeella, Hyponomeuta malinellus, Argyresthia conjugella, Sitotroga cerealella, Phthorimaea*

| Ex. | R | R¹ | R² | R³ | Y | X | nmr data (δ-values; CDCl₃; 60 MHz) |
|---|---|---|---|---|---|---|---|
| 4 | CH₃ | OC₂H₅ | S-n-C₃H₇ | CH₃ | O | S | 0.78–1.93 (9H); 2.50–3.12 (2H); 3.62 (6H); 3.86–4.47 (2H); 6.94–7.40 (1); |
| 5 | CH₃ | OCH₃ | OCH₃ | CH₃ | O | S | 1.81 (3H); 3.53–4.00 (12H); 6.96–7.38 (1H); |
| 6 | CH₃ | OC₂H₅ | NH-i-C₃H₇ | CH₃ | O | S | 1.10–1.50 (9H); 1.79 (3H); 3.30–3.88 (7H); 3.88–4.37 (2H); 7.20–7.52 (1H); |
| 7 | C₂H₅ | OC₂H₅ | OC₂H₅ | CH₃ | O | S | 1.21–1.48 (12H); 1.79 (3H); 3.91–4.38 (8H); 7.13–7.39 (1H); |
| 8 | C₂H₅ | OCH₃ | OCH₃ | CH₃ | O | S | 1.37 (6H); 1.81 (3H); 3.82 (6H); 3.95–4.30 (4H); 7.04–7.38 (1H); |
| 9 | C₂H₅ | OC₂H₅ | OC₂H₅ | CH₃ | O | O | 1.00–1.31 (12H); 1.50 (3H); 3.58–4.28 (8H); 6.88–7.13 (1H); |
| 10 | C₂H₅ | C₂H₅ | OC₂H₅ | CH₃ | O | S | 0.83–2.42 (14H); 1.72 (3H); 3.71–4.41 (6H); 7.00–7.48 (1H); |
| 11 | C₂H₅ | OC₂H₅ | NH-i-C₃H₇ | CH₃ | O | S | 1.06–1.50 (15H); 1.73 (3H); 3.20–4.36 (7H); 6.99–7.43 (1H); |
| 12 | i-C₃H₇ | OCH₃ | OCH₃ | CH₃ | O | S | 1.28 (12H); 1.68 (3H); 3.69 (6H); 4.30–4.86 (2H); 6.89–7.30 (1H); |
| 13 | i-C₃H₇ | OC₂H₅ | OC₂H₅ | CH₃ | O | S | 1.11–1.49 (18H); 1.70 (3H); 3.89–4.80 (6H); 6.89–7.30 (1H); 4.80 (6H); 6.89–7.30 (1H); |
| 14 | i-C₃H₇ | CH₃ | OC₂H₅ | CH₃ | O | S | 1.10–1.43 (12H); 1.69 (3H); 1.73 (3H); 3.78–4.88 (4H), 7.02–7.45 (1H); |
| 15 | i-C₃H₇ | C₂H₅ | OC₂H₅ | CH₃ | O | S | 0.85–1.40 (15H); 1.68 (3H); 1.70–2.31 (2H); 3.80–4.88 (4H); 6.98–7.46 (1H); |
| 16 | i-C₃H₇ | C₆H₅ | OC₂H₅ | CH₃ | O | S | 1.95–1.33 (15H); 1.63 (3H); 3.80–4.29 (4H); 7.10–8.09 (6H); |
| 17 | CH₃ | OC₂H₅ | OC₂H₅ | H | S | S | 1.37 (6H); 3.72 (6H); 4.03–4.40 (4H); 4.83–5.78 (1H); 7.18–7.62 (1H); |
| 18 | C₂H₅ | OCH₃ | OCH₃ | H | O | S | 1.36 (6H); 3.60–4.29 (10H); 5.20–5.33 (1H); 7.12–7.50 (1H); |
| 19 | C₂H₅ | OC₂H₅ | OC₂H₅ | H | O | S | 1.38 (12H); 3.91–4.38 (8H); 5.22–5.53 (1H); 7.13–7.52 (1H) |
| 20 | C₂H₅ | OC₂H₅ | OC₂H₅ | H | O | O | 1.30 (12H); 3.75–4.45 (8H); 5.18–5.61 (1H); 7.00–7.42 (1H); |
| 21 | CH₃ | OC₂H₅ | OC₂H₅ | CH₃ | S | S | 1.32 (6H); 1.78 (3H); 3.62 (6H); 3.83–4.40 (4H); 7.08–7.48 (1H); |
| 22 | CH₃ | OC₂H₅ | OC₂H₅ | C₂H₅ | S | S | 0.99–1.20 (3H); 1.36 (6H); 2.03–2.50 (2H); 3.70 (6H); 4.00–4.36 (4H); 6.60–7.48 (1H); |
| 23 | CH₃ | CH₃ | O—CH₂—C≡CH | CH₃ | O | S | 1.50–2.08 (6H); 2.50 (1H); 3.62 (6H); 4.42–4.82 (2H); 7.00–7.43 (1H) |
| 24 | CH₃ | OC₂H₅ | S-sec-C₄H₉ | CH₃ | O | S | 0.83–2.00 (14H); 3.00–4.50 (3H); 3.65 (6H); 6.50–7.45 (1H); |
| 25 | CH₃ | CH₃ | OC₂H₅ | C₂H₅ | S | S | 0.80–1.40 (6H); 1.82 (3H); 1.58–2.48 (2H); 3.59 (6H); 3.85–4.25 (2H); 6.51–7.60 (1H); |
| 26 | CH₃ | C₆H₅ | OC₂H₅ | CH₃ | O | S | 1.08–1.44 (3H); 1.68 (3H); 3.58 (6H); 3.80–4.42 (2H); 7.05–3.09 (6H); |
| 27 | CH₃ | OC₂H₅ | S-n-C₃H₇ | C₂H₅ | S | S | 0.85–1.27 (6H); 1.38 (3H); 1.50–1.90 (2H); 2.02–2.50 (2H); 2.80–3.20 (2H); 3.52–3.83 (6H); 4.01–4.41 (2H); 6.63–7.52 (1H); |
| 28 | CH₃ | OC₂H₅ | OC₃H₅ | C₂H₅ | O | S | 0.90–1.44 (9H); 1.74–2.48 (2H); 3.61 (6H); 3.80–4.45 (4H); 6.41–7.26 (1H); |
| 29 | CH₃ | C₂H₅ | OC₂H₅ | C₂H₅ | O | S | 0.90–1.46 (9H); 2.07 (4H); 3.65 (6H); 3.93–4.30 (2H); 6.65–7.47 (1H); |
| 30 | CH₃ | OCH₃ | OCH₃ | C₂H₅ | O | S | 1.02 (3H); 1.72–2.50 (2H); 3.42–3.89 (12H); 6.41–7.28 (1H); |
| 31 | CH₃ | OC₂H₅ | NH-i-C₃H₇ | C₂H₅ | O | S | 0.80–1.45 (12H); 1.80–2.52 (2H); 3.40–4.3 (9H); 6.50–7.38 (1H); |
| 32 | CH₃ | OCH₃ | OCH₃ | CH₃ | S | S | 7.03 (3H); 3.45–3.92 (12H); 6.35–7.50 (1H). |

*operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neutria, Dendrolimus pini, Thaumatopoea pityocampa, Phalera bucephala, Cheimatobia brumata, Hibernia defoliaria, Bupalus piniarius, Hyphantria cunea, Agrotis segetum, Agrotis ypsilon, Barathra brassicae, Cirphis unipuncta, Prodenia litura, Laphygma exigua, Panolis glammea, Earias insulana, Plusia gamma, Alabana argillacea, Lymantria dispar., Lymantria monacha, Pieris brassicae,* and *Aporia crataegi;*

Coleoptera order: for example *Blitophaga undata, Melanotus communis, Limonius californicus, Agriotes lineatus, Agriotes obscurus, Agrilus sinuatus, Meligethes aeneus, Atomaria linearis, Epilachna varivestris, Phyllopertha horticola, Popilla japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Psylloides chrysocephala, Diabrotica 12-punctata, Cassida nebulosa, Bruchus lentis, Bruchus refimanus, Bruchus pisorum, Sitona lineatus, Otiorrhynchus sulcatus, Otirrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;*

Diptera order, for example *Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae,* and *Pegomya hyoscyami;*

Hymenoptera order, for example *Athalia rosae, Hoplocampa minuta, Monomorium pharaonis, Solenopsis geminata,* and *Atta sexdens;*

Heteroptera order, for example *Nezara viridula, Eurygaster integriceps, Blissus leucopterus, Dysdercus cingulatus, Piesma quadrata,* and *Lygus pratensis;*

Homoptera order, for example *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Pysaulacorthum pseudosolani, Acrythosiphon onobrychis, Macrosiphon rosae, Megoura viciae, Schizoneura lanuginosa, Eriosoma lanigerum, Pemphigus bursarius, Dreyfusia nordmannianae, Dreyfusia piceae, Adelges laricis,* and *Viteus vitifolii;*

Isoptera order, for example *Reticulitermes lucifugus;*

Acarina of the Arachnida order, for example *Ixodes recinus, Ornithodorus moubata, Amblyomma americanum, Dermacentor silvarum,* and *Bosphilus microplus.*

The compounds according to the invention may be successfully used as pesticides in the crop protection, hygiene, stores protection and veterinary sectors. Either the pests or the objects to be protected against pest attack may be treated with an effective amount of one or more of the active ingredients according to the invention.

The active ingredients may be applied as such, in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared form emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of linginsulfonic acid, naphthalenesulfonic acids, phenosulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The active ingredient concentration in the finished composition may vary within a fairly wide range. The concentration is generally from 0.0001 to 10%, preferably from 0.01 to 1%.

The active ingredients may also be successfully used in the ultra-low volume method (ULV), where it is possible to apply formulations containing up to 95% of active ingredient or 100% active ingredient on its own.

Examples of possible formulations are as follows.

I. 500 g O,O-diethyl-O-(2-methyl-2-O,O-dimethylphosphonyl)-vinylthiophosphate; 40 g calcium dodecylbenzene sulfonate; 60 g ethoxylated oleic acid monoethanolamide; xylene makeup to 1,000 ml.

II. 20 parts by weight of O,O-diethyl-O-(2-methyl-2-O,O-dimethylphosphonyl)-vinylthiophosphate is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

III. 20 parts by weight of O-ethyl-S-n-propyl-O-(2-methyl-O,O-dimethylphosphonyl)-vinyldithiophosphate is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

IV. 3 parts of by weight of O,O-diethyl-O-(2-methyl-2-O,O-diisopropylphosphonyl)-vinylphosphate is intimately mixed with 97 parts by weight of particulate kaolin. A dust is obtained containing 3% by weight of the active ingredient.

V. 30 parts by weight of O-ethyl-N-isopropyl-O-(2-methyl-2-O,O-dimethylphosphonyl)-vinylthiophosphonic acid amide is intimately mixed with a mixture consisting of 92 parts by weight of powdered silica gel and 8 parts by weight of paraffin oil which has been sprayed onto the surface of this silica gel. A formulation of the active ingredient is obtained having good adherence.

There may be added to the compositions or individual active ingredients (if desired, immediately before use (tankmix)) oils of various types, herbicides, fungicides, nematocides, insecticides, and bactericides. These agents may be added to the agents according to the invention in a weight ratio of from 10:1 to 1:10.

Examples of agents which may be added are 1,2-dibromo-3-chloropropane, 1,3-dichloropropene, 1,3-dichloropropene+1,2-dichloropropane, 1,2-dibromoethane, 2-sec-butylphenyl-N-methyl carbamate, o-chlorophenyl-N-methyl carbamate, 3-isopropyl-5-methylphenyl-N-methyl carbamate, o-isopropoxyphenyl-N-methyl carbamate, 3,5-dimethyl-4-methylmercaptophenyl-N-methyl carbamate, 4-dimethylamino-3,5-xylyl-N-methyl carbamate, 2-(1,3-dioxolan-2-yl)-phenyl-N-methyl carbamate, 1-naphthyl-N-methyl carbamate, 2,3-dihydro-2,2-dimethylbenzofuran-7-yl-N-methyl carbamate, 2,2-dimethyl-1,3-benzodioxol-4-yl-N-methyl carbamate, 2-dimethylamino-5,6-dimethyl-4-pyrimidinyldimethyl carbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N',N'-dimethylformamidine, tetrachlorothiophene, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethylphosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoroamidate, O,O-diethyl-O-[p-(methylsulfynyl)-phenyl]-phosphorothioate, O-ethyl-S-phenylethylphosphonodithioate, O,O-diethyl-[2-chloro-1-(2,4-dichlorophenyl)-vinyl]-phosphate, O,O-dimethyl-[2-chloro-1-(2,4,5-trichlorophenyl)]-vinylphosphate, O,O-dimethyl-S-(1-phenyl)-ethyl acetate phosphorodithioate, bis-(dimethylamino)-fluorophosphine oxide, octamethylpyrophosphoramide, O,O,O,O-tetraethyldithiopyrophosphate, S-chloromethyl-O,O-diethylphosphorodithioate, O-ethyl-S,S-dipropylphosphorodithioate, O,O-dimethyl-O-2,2-dichlorovinyl phosphate, O,O-dimethyl-1,2-dibromo-2,2-dichloroethyl phosphate, O,O-dimethyl-2,2,2-trichloro-1-hydroxyethyl phosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorodithioate, O,O-dimethyl-S-(2-ethylsulfynylethyl)-phosphorothioate, O,O-diethylthiophosphoryliminophenyl acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiodiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-ylmethyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoramidothioate, O,S-dimethyl-N-acetylphosphoramidothioate, γ-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide.

The following examples demonstrate the biological action. The agents used for comparison purposes are O,O-dimethyl-S-(1,2-dicarbethoxyethyl)-dithiophosphoric acid ester (A) (German 847,897) and O,O-dimethyl-O-(2-carbomethoxy-2-methylvinyl)-thiophosphoric acid ester (B) (German Laid-Open Application DOS 1,643,779).

EXAMPLE A

Contact action on cotton stainers (*Dysdercus intermedius*)

Petri dishes 10 cm in diameter are lined with 1 ml of acetonic solutions of the active ingredients.

After the solvent has evaporated, 20 larvae in the penultimate stage are placed in the dishes and the effect is registered after 24 hours.

| Active ingredient from Ex. no. | Amount of active ingredient per dish (in mg) | Mortality (in %) |
|---|---|---|
| 1 | 0.001 | 100 |
| 2 | 0.002 | 100 |
| 5 | 0.005 | 80 |
| 7 | 0.01 | 100 |
| 8 | 0.002 | 100 |
| 10 | 0.002 | 100 |
| Comparative agent A | 0.02 | 100 |
|  | 0.01 | 60 |

EXAMPLE B

Contact action on red flour beetle (*Tribolium castaneum*); resistant strain

Circular filter papers 7 cm in diameter are impregnated with acetonic solutions of the active ingredients. After the solvent has evaporated, red flour beetles are placed on the treated filter papers inside glass rings 4.5 cm in diameter.

The mortality is determined after 24 hours.

| Active ingredient from Ex. no. | Amount of active ingredient per dish (in mg) | Mortality (in %) |
|---|---|---|
| 1 | 0.1 | 100 |
| 2 | 0.2 | 100 |
| 4 | 0.5 | 100 |
| 5 | 0.1 | 100 |
| 6 | 0.25 | 100 |
| 7 | 0.2 | 100 |
| 10 | 0.1 | 100 |
| Comparative agent A | 1.0 | ineffective |

EXAMPLE C

Contact action on bean aphids (*Aphis fabae*); spray experiment

Potted bean plants (*Vicia faba*) heavily infected with aphid colonies are sprayed to runoff in a spray cabinet with aqueous formulations of the active ingredients.

Assessment takes place after 24 hours.

| Active ingredient from Ex. no. | Concentration of aqueous active ingredient formulation (in %) | Mortality (in %) |
|---|---|---|
| 1 | 0.01 | 100 |
| 2 | 0.005 | 100 |
|  | 0.002 | 80 |
| 5 | 0.002 | 100 |
| Comparative agent A | 0.01 | 80 |
| Comparative agent B | 0.02 | 80 |

EXAMPLE D

Contact action on ticks (*Ornithodorus moubata*)

Ticks of the third larval stage are placed in a paper bag which is then dipped for 3 seconds in the emulsion under examination. The bags are then suspended. After 48 hours the action on the ticks is assessed.

| Active ingredient from Ex. no. | Concentration of active ingredient emulsion (in %) | Mortality (in %) |
|---|---|---|
| 1 | 0.01 | 100 |
| 2 | 0.0005 | 100 |
| 4 | 0.005 | 100 |
| 5 | 0.001 | 80 |
| 6 | 0.001 | 80 |
| 7 | 0.0025 | 100 |
| 8 | 0.0025 | 100 |
| 9 | 0.001 | 100 |
| 10 | 0.01 | 100 |
| Comparative agent A | 0.1 | 80 |
| Comparative agent B | 0.1 | 80 |

EXAMPLE E

Action on root-knot nematodes (*Meloidogyne incognita*)

200 g of compost heavily infected with root-knot nematodes (*Meloidogyne incognita*) is carefully mixed with 30 ml of aqueous formulations of the active ingredients; the soil treated in this manner is then filled into 300 ml plastic pots. 2 cucumber seeds are placed in each pot and the pots are kept under greenhouse conditions (temperature: 22° C.).

The extent to which the roots have been attacked is assessed after 6 weeks.

| Active ingredient from Ex. 4 | 0.05% | no gall formation |
|---|---|---|
| Comparative agent A | 0.1% | heavy gall infection |
| Comparative agent B | 0.1% | heavy gall infection |

EXAMPLE F

Contact action on granary weevils (*Sitophilus granarius*)

Petri dishes 10 cm in diameter are lined with acetonic solutions of the active ingredients. After the solvent has evaporated, 100 granary weevils are placed in each of the dishes. After 4 hours, the weevils are transferred to untreated cardboard dishes. The number of animals still able to leave this vessel is then counted.

| Active ingredient from Ex. no. | Amount of active ingredient per dish (in mg) | Mortality (in %) |
|---|---|---|
| 2 | 0.1 | 100 |
|  | 0.05 | 80 |

-continued

| Active ingredient from Ex. no. | Amount of active ingredient per dish (in mg) | Mortality (in %) |
|---|---|---|
| 5 | 0.02 | 100 |
| 6 | 0.1 | 100 |
| 7 | 0.2 | 100 |
| 8 | 0.1 | 100 |
| Comparative agent B | 0.25 | 80 |

EXAMPLE G

Contact action on oriental cockroaches (*Blatta orientalis*)

The bottom of 1 liter preserving jars is treated with acetonic solutions of the active ingredients.

After the solvent has evaporated, 5 adult cockroaches are placed in each jar.

The kill is determined after 48 hours.

| Active ingredient from Ex. no. | Amount of active ingredient per jar (in mg) | Mortality (in %) |
|---|---|---|
| 1 | 0.2 | 100 |
|   | 0.1 | 80 |
| 2 | 0.1 | 100 |
| 4 | 0.2 | 100 |
| 5 | 0.2 | 100 |
|   | 0.1 | 80 |
| 7 | 0.2 | 100 |
| 10 | 0.1 | 100 |
| Comparative agent B | 0.2 | 80 |
|   | 0.1 | 40 |

EXAMPLE H

Contact action and effect of ingested food on caterpillars of the diamondback moth (*Plutella maculipennis*)

Leaves of young cabbage plants are dipped for 3 seconds in aqueous emulsions of the active ingredients, and, after briefly having allowed excess liquid to drip off, are placed on a moist filter paper in a Petri dish. 10 caterpillars of the 4th larval stage are then placed on each leaf.

The kill in % is determined after 48 hours.

| Active ingredient from Ex. no. | Concentration of aqueous active ingredient solution (in %) | Mortality (in %) |
|---|---|---|
| 1 | 0.025 | 100 |
|   | 0.01 | 80 |
| 2 | 0.01 | 100 |

-continued

| Active ingredient from Ex. no. | Concentration of aqueous active ingredient solution (in %) | Mortality (in %) |
|---|---|---|
|   | 0.005 | 90 |
|   | 0.002 | 80 |
| 4 | 0.025 | 100 |
|   | 0.01 | 80 |
| 5 | 0.01 | 100 |
|   | 0.005 | 80 |
| 7 | 0.025 | 100 |
|   | 0.01 | 80 |

We claim:

1. A phosphoric acid derivative of the formula $$\begin{array}{c} RO \diagdown \overset{Y}{\underset{\parallel}{P}} \\ RO \diagup \end{array} - C = CH - O - \overset{X}{\underset{\parallel}{P}} \diagdown \overset{R^1}{R^2} \quad I,$$

where R denotes linear or branched alkyl of a maximum of 6 carbon atoms, $R^1$ denotes linear or branched alkyl or alkoxy of a maximum of 6 carbon atoms, linear or branched alkynyloxy of a maximum of 4 carbon atoms, phenyl, phenyl mono- or polysubstituted by halogen or alkyl of 1 to 4 carbon atoms, or benzyloxy, $R^2$ denotes alkoxy, alkylthio, alkylamino or dialkylamino (alkyl in these radicals being linear or branched and of a maximum of 6 carbon atoms), linear or branched alkynyloxy of a maximum of 4 carbon atoms, or benzyloxy, $R^3$ denotes hydrogen or linear or branched alkyl of a maximum of 3 carbon atoms, X denotes oxygen or sulfur, and Y denotes oxygen or sulfur.

2. A phosphoric acid derivative as claimed in claim 1, wherein R and $R^3$ are methyl, $R^1$ and $R^2$ are methoxy or ethoxy, X is sulfur, and Y is oxygen.

3. The compound of the formula $$\begin{array}{c} CH_3O \diagdown \overset{O}{\underset{\parallel}{P}} \\ CH_3O \diagup \end{array} - C = CH - O - \overset{S}{\underset{\parallel}{P}} \diagdown \overset{OCH_3}{OCH_3} \text{ .}$$

4. The compound of the formula $$\begin{array}{c} CH_3O \diagdown \overset{O}{\underset{\parallel}{P}} \\ CH_3O \diagup \end{array} - C = CH - O - \overset{S}{\underset{\parallel}{P}} \diagdown \overset{OC_2H_5}{OC_2H_5} \text{ .}$$

5. A pesticide comprising a solid or liquid carrier and a phosphoric acid derivative of claim 1 as active component.

6. A process for combatting pests, wherein the pests or the objects to be protected against pest attack are treated with an effective amount of a phosphoric acid derivative of claim 1.

* * * * *